United States Patent
De Canha et al.

(10) Patent No.: US 10,695,283 B2
(45) Date of Patent: Jun. 30, 2020

(54) **EXTRACT OF *GREYIA RADLKOFERI* AND USE THEREOF**

(71) Applicants: UNIVERSITY OF PRETORIA, Pretoria (ZA); UNIVERSITY OF KWAZULU-NATAL, Durban (ZA)

(72) Inventors: Marco Nuno De Canha, Pretoria (ZA); Namrita Lall, Pretoria (ZA); Ahmed Hussein, Cairo (EG); Elizabeth Mogapi, Midrand (ZA); Indres Moodley, Durban (ZA)

(73) Assignees: UNIVERSITY OF PRETORIA, Pretoria (ZA); UNIVERSITY OF KWAZULU-NATAL, Durban (ZA)

( * ) Notice: Subject to any disclaimer, the term of this patent is extended or adjusted under 35 U.S.C. 154(b) by 78 days.

(21) Appl. No.: 15/816,544

(22) Filed: Nov. 17, 2017

(65) Prior Publication Data
US 2018/0071204 A1 Mar. 15, 2018

Related U.S. Application Data

(62) Division of application No. 14/400,645, filed as application No. PCT/IB2013/054054 on May 17, 2013, now abandoned.

(30) Foreign Application Priority Data

May 18, 2012 (ZA) ................. 2012/03648

(51) Int. Cl.
| | | |
|---|---|---|
| *A61K 36/00* | (2006.01) | |
| *A61K 8/97* | (2017.01) | |
| *A61Q 19/02* | (2006.01) | |
| *A61K 36/77* | (2006.01) | |
| *A61Q 19/00* | (2006.01) | |

(52) U.S. Cl.
CPC ............... *A61K 8/97* (2013.01); *A61K 36/77* (2013.01); *A61Q 19/00* (2013.01); *A61Q 19/02* (2013.01); *A61K 2236/39* (2013.01)

(58) Field of Classification Search
None
See application file for complete search history.

(56) References Cited

U.S. PATENT DOCUMENTS

2007/0011762 A1 1/2007 Vinson et al.

FOREIGN PATENT DOCUMENTS

WO 2007/098873 A1 9/2007

OTHER PUBLICATIONS

Mapunya et al. ("Tyrosinase activity of Greyia Flanaganii (Bolus) constituents" Aug. 15, 2011 (Aug. 15, 2011), Phytomedicine: International Journal of Phytoherapy 18, Nr. 11, pp. 1006-1102), see also within submitted IDS) (Year: 2011).*
Bohm et al. ("Flavonoids and Affinities of Greyiaceae with a Discussion of the Occurence of B-Ring Deoxyflavonioids in Dicotyledonous Families", Syystematic Botany, American Society of Plant Taxonomists, Kent, Oh, US , vol. 17, No. 2, Jan. 1, 1992 (Feb. 1, 1992), pp. 272-281, within submitted IDS) (Year: 1992).*
Mapunya, M.B., et al, "Tyrosinase activity of Greyia flanaganii (Bolus) constituents", Phytomedicine 18 (2011) 1006-1012.
Bohm, Bruce A., et al, "Flavonoids and Affinities of Greyiaceae with a Discussion of the Occurrence of B-Ring Deoxyflavonoids in Dicotyledonous Families", Systematic Botany (1992), 17(2): pp. 272-281.

* cited by examiner

*Primary Examiner* — Michael Barker
*Assistant Examiner* — Randall Winston
(74) *Attorney, Agent, or Firm* — Nath, Goldberg & Meyer; Joshua M. Goldberg

(57) ABSTRACT

This invention relates to the isolation, and use of a plant extract in the treatment of skin hyper-pigmentation. More particularly, this invention relates to the isolation of a tyrosinase inhibitor in an extract of plant matehal from the *Greyia radlkoferi* (*G. radlkoferi*) plant, the extract including 5,7-dihidroxyflavone[(2S)-pinocembrin]; 2',6'-dihydroxy-4'-methoxydihydrochalcone; 2',4',6'-trihydroxyhydrochalcone; 3,5,7-trihydroxyflavone and 4',5'7-thhydroxyisoflavone.

4 Claims, No Drawings

EXTRACT OF *GREYIA RADLKOFERI* AND USE THEREOF

This is a Divisional Application of U.S. patent application Ser. No. 14/400,645, filed Nov. 12, 2014, an application which is a 371 of PCT/IB2013/054054 with an international filing date of May 17, 2013 which application claims the benefit of South African Application No. 2012/03648, filed on May 18, 2012, the disclosures of each of which are incorporated herein in their entirety by reference.

This invention relates to the isolation and use of a plant extract in the treatment of skin hyper-pigmentation. More particularly, this invention relates to the isolation of a tyrosinase inhibitor from plant material of the *Greyia radlkoferi* (*G. radlkoferi*) plant.

Skin hyper-pigmentation is a condition caused by the overproduction of melanin, a pigment present in about 10% of melanocytes. The copper containing mono-oxygenase enzyme referred to as 'tyrosinase' is a key enzyme in the synthesis of melanin, due to melanin biosynthesis being regulated by the tyrosinase enzyme which is responsible for catalysing the rate limiting step in the biosynthetic pathway. Over-activity of tyrosinase leads to over production of melanin which ultimately leads to hyper-pigmentation of the skin. Hyper-pigmentation of the skin can be attributed to excessive exposure to UV light, adverse reactions to drugs and also occurs during ageing.

Inhibition of the tyrosinase enzyme is therefore a well known target for the treatment of skin hyper-pigmentation. Many known products used for the treatment of skin hyper-pigmentation have been associated with toxicity and other adverse effects. These known products include agents such as hydroquinone, kojic acid, arbutin, glabridin and isoliquiritigenin. Some cosmetic products containing these agents have shown to be cytotoxic and mutagenic in humans. In addition to being cytotoxic and mutagenic, known treatments for skin hyper-pigmentation have also been known to cause specific and unwanted side effects, as explained in more detail below.

Hydroquinone has been largely acknowledged in medical research and literature as the primary topical ingredient for inhibition of melanin production. It has been known to cause skin irritation, and fears exist about perceived carcinogenic properties. It has accordingly been banned from use as a skin lightening agent in the member states of the European Union, and is regulated by the FDA in the United States of America insofar as over the counter sales are concerned.

Kojic acid is a by-product obtained from fermenting rice in the production of Japanese rice wine, or sake as it is also commonly known. It has been touted as an effective inhibitor of melanin production, and is widely accepted as one of the most effective pure products indicated in the treatment of skin hyper pigmentation. However, the use of kojic acid in the treatment of skin hyper-pigmentation has become more and more controversial, due to certain studies suggesting that kojic acid might be carcinogenic, and it has subsequently been banned from cosmetic use in Korea and Japan. Over and above the suggested carcinogenic potential of kojic acid, it has also been found to be a potential cause of irritant contact dermatitis; is allergenic; has a high sensitising potential; and a high frequency of contact sensitivity. Kojic acid has also been found to discolour to a brown colour upon exposure to sunlight and ambient air, which also leads to decreased efficiency. Kojic dipalmitate has been suggested as an alternative to kojic acid to overcome the disadvantages associated with kojic acid, but tests have revealed that kojic dipalmitate does not exhibit the same effectiveness as kojic acid.

A further known compound indicated in the treatment of skin hyper-pigmentation is arbutin, which is derived from various berry-plants, including mulberry, cranberry and blueberry. It is indicated as having skin lightening properties, but has been associated with skin irritation.

Glabridin and isoliquiritigenin, both extracted from liquorice (*Glycyrrhiza glabra*) have also been found to exhibit skin lightening properties, but do not penetrate the skin effectively, and are both unstable when used in formulations.

Object of the Invention

It is accordingly an object of the current invention to provide a tyrosinase inhibitor with which the above disadvantages experienced with known tyrosinase inhibitors and other treatments of skin hyper-pigmentation could at least partially be overcome, or to provide a relatively more useful, environmentally friendly, organic alternative to the known tyrosinase inhibitors in a cost efficient manner.

SUMMARY OF THE INVENTION

According to a first aspect of the invention there is provided a method for preparing a plant extract having tyrosinase inhibitor activity for the treatment of skin hyper-pigmentation, the method including the steps of:
  drying leaves of *Greyia radlkoferi* (*G. radlkoferi*);
  pulverising the dried leaves;
  mixing the pulverised leaves with a solvent to allow phenolic compounds to leach into the solvent; and
  removing the pulverised leaves from the solvent, such that the plant extract remains in the solvent.

Further according to the invention, the solvent may be selected from the group consisting of water and ethanol.

The step of mixing the pulverised leaves with solvent may include the further step of agitating the mixture to improve leaching of phenolic compounds from the leaves into the solvent.

The step of separating the pulverised leaves from the solvent may include the step of passing the solvent through a vacuum filter system.

Further according to the invention the method includes the step of adding a preservative to the plant extract. Preferably, the preservative is in the form of 1% of a mixture of phenoxyethanol and ethylhexylglycerin added to the plant extract on a weight per weight basis.

Further according to the invention, the method includes the further step of preparing the plant extract in a topical dosage form selected from the group consisting of creams; lotions; aqueous solutions; balms; sunscreens; skin-oils and ointments.

According to a second aspect of the invention there is provided a plant extract for the treatment of skin hyper-pigmentation by inhibiting tyrosinase activity prepared in accordance with a method of the first aspect of the invention, characterised in that the extract includes 5,7-dihidroxyflavone[(2S)-pinocembrin]; 2',6'-dihydroxy-4'-methoxydihydrochalcone; 2',4',6'-trihydroxyhydrochalcone; 3,5,7-trihydroxyflavone and 4',5'7-trihydroxyisoflavone.

Further according the invention, the plant extract displays tyrosinase inhibitory activity by exhibiting a 50% inhibitory concentration ($IC_{50}$) ranging from 17.96 µg/ml to 32.62 µg/ml when using L-tyrosine and dihydroxyphenylalanine (DOPA) as substrates.

According to a third aspect of the invention there is provided for use of the plant extract according to the first and second aspects of the invention in the preparation of a topical dosage form for use in a method of treating a patient suffering from skin hyper-pigmentation.

According to a fourth aspect of the invention there is provided a topical dosage form selected from any one of the group consisting of a cream; lotion; aqueous solution; balm; sunscreen; skin-oil; and an ointment, for the treatment of skin hyper-pigmentation comprising a plant extract according to the second aspect of the invention, in a suitable dermatologically acceptable carrier.

DESCRIPTION OF A PREFERRED EMBODIMENT OF THE INVENTION

A preferred embodiment of the invention will now be described in more detail with reference to a non-limiting example.

In accordance with a preferred embodiment of the invention, a method for preparing a plant extract having tyrosinase inhibitor activity for the treatment of skin hyper-pigmentation includes the steps of:

air drying leaves of *G. radlkoferi* away from exposure to the sun at room temperature;
pulverising the dried leaves;
mixing 25 g of the pulverised leaves with 200 ml solvent to form a mixture;
subjecting the mixture to shaking for 48 hours to allow phenolic compounds to leach into the solvent; and
separating the pulverised leaves from the solvent through vacuum filtration by using a Buchner funnel to form the plant extract.

The solvent used to mix with the pulverised leaves is preferably 70% ethanol. Deionised distilled water could be used as an alternative solvent to ethanol to provide an organic extract.

The plant extract is preserved by adding a preservative in the form of 1% of a mixture of phenoxyethanol and ethylhexylglycerin added to the plant extract on a weight per weight basis, after which it is stored in a cold room at 4° Celsius. The preservative challenge test indicated that the preservative that was added to the extract was successful at inhibiting the growth of certain microorganisms, including *Eschericia coli, Staphylococcus aureus, Pseudomonas aureginosa, Candida albicans* and *Aspergillus*.

To determine the constituent compounds of the plant extract, the plant extract is subjected to bioassay guided fractionation. In doing so, approximately 59.5 g of the plant extract is dissolved in a minimal amount of acetone solvent and mixed with silica gel. The mixture is then left to dry until formation of a fine powder. This fine powder is then chromatographed on a silica gel column using hexane (Hex): ethylacetate (EtOAc) mixtures of increasing polarity (100:0 Hex to 0:100 EtOAc). A total of 40 preliminary fractions of approximately 500 ml each are collected. The column is then washed with 2 litres of 100% methanol (MeOH). The preliminary fractions are then concentrated using a rotor vapour and spotted on a thin layer chromatography (TLC) plate which is then developed with dichoromethane (DCM:MeOH) 95:5, viewed under UV light and immersed in a vanillin solution (7.5 g vanillin, 250 ml EtOH and 5 ml concentrated 98% sulphuric acid ($H_2SO_4$)) and heated to detect compounds not absorbing under UV light. Fractions which contained a similar profile of compounds on the TLC plate are combined and concentrated using a rotor vapour. These fractions are then further chromatographed for isolation and identification of bioactive compounds. Following this step, certain fractions are then subjected to a series of sephadex columns LH-20 eluted with 100% EtOH and then washed with 100% MeOH to yield Compound C1. Other fractions are firstly subjected to series of sephadex columns using 100% MeOH as a solvent to yield certain fractions, one of which is also subjected to a sephadex column using 100% MeOH to obtain sub-fractions. One of these sub-fractions is subjected to a preparative TLC eluted with DCM:MeOH (9:1) to isolate Compound C2. A further fraction is subjected to a sephadex column using 100% MeOH, from this Compound C3 is isolated. Compounds C4 and C5 are isolated using similar methods.

The end products of the bioassay guided fractionation are the isolation of five known phenolic compounds, namely 5,7-dihidroxyflavone[(2S)-pinocembrin] (C1); 2',6'-dihydroxy-4'-methoxydihydrochalcone (C2); 2',4',6'-trihydroxyhydrochalcone (C3); 3,5,7-trihydroxyflavone (C4) and 4',5'7-trihydroxyisoflavone (C5), all of which have been shown to exhibit individual tyrosinase inhibitory capabilities, as well as a synergistic action in the inhibition of tyrosinase activity.

These compounds have previously been extracted from other plants and their tyrosinase inhibitory qualities have been documented before. *G. radlkoferi* is however the first plant wherein ail five of these compounds (C1 to C5) have been found in one single plant, which is also indigenous to South Africa.

These individual phenolic compounds exhibit differing levels of tyrosinase inhibition when used in isolation. C3 (2',4', 6'-trihydroxydihydrochalcone) exhibits an 50% inhibitory concentration ($IC_{50}$) value of 17.86 µg/ml, C4 (3,5,7-trihydroxyflavone, also known as galangin) exhibits an $IC_{50}$ value of 2.23 µg/ml with more than 50% of melanin being inhibited at concentrations as low as 3.1 µg/ml. C2 (2',6'-dihydroxy-4'-methoxydihydrochalcone, also known as genistein) exhibits an $IC_{50}$ value of 21.42 µg/ml and 20% melanin reduction is observed at 3.125 µg/ml.

The plant extract from *G. radlkoferi* shows significant inhibitory activity by exhibiting a $IC_{50}$ value of 17.96 µg/ml when L-tyrosine and DOPA are used as substrates, which $IC_{50}$ compares favourably against known compounds like kojic acid (3.78 µg/ml), isoliquirtigenin (896.88 µg/ml), arbutin (149 µg/ml) and an extract from *Greya flanaganii* (32.62 µg/ml).

The plant extract also exhibits increased skin even tone at 3% in a clinical study known as the spot reduction and skin even tone test, whereas *G. flanaganii* does not show the same effectiveness at 3%.

The inhibition of hyper-pigmentation is not restricted to inhibition at the enzyme level but melanin inhibition can also be achieved in vitro by the inhibition of melanin release by melanocyte cells. In conducting this test, the plant extract was compared with an arbutin positive control, and 50% melanin reduction in melanocytes was observed with cells being viable at concentrations up to 50 µg/ml.

The plant extract is non-mutagenic even when tested at a relatively high concentration of 5.0 mg/ml.

Microbial and heavy metal analysis investigation of the cosmeceutical actives of *G. radlkoferi* shows absence of any microbial contamination and heavy metals such as lead, arsenic and mercury.

The plant extract according to the invention is to be included in a topical dosage form for the treatment of skin hyper-pigmentation, formulated to provide the application of approximately 5 ml plant extract per 20 cm$^2$ of skin affected by skin hyper-pigmentation. This topical dosage form is prepared as a cream; lotion; aqueous solution; balm; sunscreen; skin-oil; and/or an ointment in a suitable dermatologically acceptable carrier such as aqueous cream.

One of the disadvantages that has been recorded with known compounds for the treatment for skin hyper-pigmentation, like arbutin, is skin irritation. This disadvantage is accordingly overcome by the plant extract and method for extracting same according to the invention.

The plant extract also shows increased skin penetration, and accordingly overcomes the disadvantage of decreased skin penetration shown by other known compounds like glabridin and isoliquiritigenin which can be extracted from the liquorice plant.

Serious disadvantages, including cytotoxicity, mutagenicity and carcinogenicity, that are associated with hydroquinone and kojic acid, both known treatments of skin hyper-pigmentation, are also overcome by the plant extract according to the invention.

It will be appreciated that variations in details are possible with a plant extract and method of extracting the same, for use in the treatment of skin hyper-pigmentation according to the invention, without departing from the scope of the appended claims.

The invention claimed is:

1. A method of treating skin hyper-pigmentation by inhibiting tyrosinase activity, in a patient in need thereof the method comprising:
   administering to the patient an effective amount of a composition comprising an extract from leaves of *Greyia radlkoferi* comprising 5,7-dihidroxyflavone [(2S)-pinocembrin]; 2',6'-dihydroxy-4'-methoxydihydrochalcone; 2',4',6'-trihydroxyhydrochalcone; 3,5,7-trihydroxyflavone and 4',5'7-trihydroxyisoflavone.

2. The method of claim 1, wherein the composition displays tyrosinase inhibitory activity by exhibiting a 50% inhibitory concentration ($IC_{50}$) ranging from 17.96 µg/ml to 32.62 µg/ml when using L-tyrosine and dihydroxyphenylalanine (DOPA) as substrates.

3. The method of claim 1, further comprising preparing the composition in a topical dosage form.

4. The method of claim 3, wherein the topical dosage form is selected from any one of the group consisting of: a cream; lotion; aqueous solution; balm; sunscreen; skin-oil; and an ointment, in a suitable dermatologically acceptable carrier.

* * * * *